(12) United States Patent
Kulprathipanja

(10) Patent No.: US 7,241,918 B1
(45) Date of Patent: Jul. 10, 2007

(54) SEPARATION OF CITRIC ACID FROM GLUCONIC ACID IN FERMENTATION BROTH USING A WEAKLY OR STRONGLY BASIC ANIONIC EXCHANGE RESIN ADSORBENT

(75) Inventor: Santi Kulprathipanja, Inverness, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/392,095

(22) Filed: Mar. 18, 2003

(51) Int. Cl.
*C07C 51/42* (2006.01)
*C07C 59/265* (2006.01)

(52) U.S. Cl. ...................... 562/584; 562/580
(58) Field of Classification Search ............... 562/580, 562/584; 435/136, 144
See application file for complete search history.

(56) References Cited

U.S. PATENT DOCUMENTS

| | | | |
|---|---|---|---|
| 2,664,441 A | 12/1953 | Owens et al. | 260/527 |
| 3,040,777 A | 6/1962 | Carson et al. | 137/625.15 |
| 3,086,928 A | 4/1963 | Schultz | 204/72 |
| 3,983,170 A | 9/1976 | Sumikawa et al. | 562/580 |
| 4,323,702 A | 4/1982 | Kawabata et al. | 562/580 |
| 4,851,573 A | 7/1989 | Kulprathipanja et al. | 562/580 |
| 4,851,574 A | 7/1989 | Kulprathipanja et al. | 562/580 |
| 5,068,419 A * | 11/1991 | Kulprathipanja et al. | 562/580 |
| 5,712,131 A * | 1/1998 | Felman et al. | 435/136 |

FOREIGN PATENT DOCUMENTS

| | | |
|---|---|---|
| EP | 151470 | 1/1985 |
| GB | 868926 | 6/1957 |
| WO | WO 95/32301 | * 11/1995 |

OTHER PUBLICATIONS

A.J. DeRosset et al., Separation of $C_8$ Aromatics by Adsorption A.J. DeRosset et al., presented at the American Chemical Society, Los Angeles, CA Mar. 29-Apr. 2, 1971.

* cited by examiner

*Primary Examiner*—Taylor Victor Oh
(74) *Attorney, Agent, or Firm*—Maryann Maas

(57) ABSTRACT

Citric acid is separated from a fermentation broth containing gluconic acid by using an adsorbent comprising a water-insoluble, macroreticular or gel, strongly or weakly basic anionic exchange resin possessing quaternary or tertiary amine functional groups, said a anionic exchange resin having a cross-linked acrylic or styrene resin matrix and a desorbent comprising water or dilute sulfuric acid. The pH of the feed is maintained below the first ionization constant ($pKa_1$) of citric acid to maintain selectivity.

18 Claims, 3 Drawing Sheets

SEPARATION OF CITRIC ACID FROM GLUCONIC ACID IN FERMENTATION BROTH USING A WEAKLY OR STRONGLY BASIC ANIONIC EXCHANGE RESIN ADSORBENT

FIELD OF THE INVENTION

The field of art of this invention is the solid bed adsorptive separation of citric acid from fermentation broths containing citric acid, an organic acid such as gluconic acid or aconitic acid, carbohydrates, amino acids, proteins and salts. More specifically, the invention relates to a process for separating citric acid from gluconic acid which process employs an adsorbent comprising particular polymers which selectively adsorb citric acid from a fermentation mixture containing citric acid and gluconic acid.

BACKGROUND OF THE INVENTION

Citric acid is used as a food acidulant, and in pharmaceutical, industrial and detergent formulations. The increased popularity of liquid detergents formulated with citric acid has been primarily responsible for growth of worldwide production of citric acid to about 700 million pounds per year which is expected to continue in the future.

Citric acid is produced by a submerged culture fermentation process which employs molasses as feed and the microorganism, *Aspergillus-Niger*. In some applications, the fermentation product will contain organic acids such as gluconic acid or aconitic acid carbohydrates, amino acids, proteins and salts as well as citric acid, which must be separated from the fermentation broth.

There are two historical technologies employed for the separation of citric acid from fermentation broths. The first disclosed in U.S. Pat. No. 3,086,928 involves calcium salt precipitation of citric acid. The resulting calcium citrate is acidified with sulfuric acid. In the second process, citric acid is extracted from the fermentation broth with a mixture of trilaurylamine, n-octanol and a $C_{10}$ or $C_{11}$ isoparaffin. Citric acid is reextracted from the solvent phase into water with the addition of heat. Both techniques, however, are complex, expensive and they generate a substantial amount of waste for disposal.

The patent literature has suggested a possible third method for separating citric acid from the fermentation broth, which involves membrane filtration to remove raw materials or high molecular weight impurities and then adsorption of contaminants onto a nonionic resin based on polystyrene or polyacrylic resins and collection of the citric acid in the rejected phase or raffinate and crystallization of the citric acid after concentrating the solution, or by precipitating the citric acid as the calcium salts then acidifying with $H_2SO_4$, separating the $CaSO_4$ and contacting cation- and anion-exchangers. This method, disclosed in EP 151,470, is also a rather complex and lengthy method for separating the citric acid. In contrast, my method makes it possible to separate the citric acid in a single step and recover the citric acid in a much simplified process. Succinctly stated, the citric acid is adsorbed selectively by the adsorbent and purified citric acid is desorbed by a desorbent, for example, water or a dilute acid, sulfuric acid, hydrochloric acid, nitric acid, or phosphoric acid.

SUMMARY OF THE INVENTION

This invention relates to a process for adsorbing citric acid from a fermentation broth containing an organic acid selected from the group consisting of gluconic acid and aconitic acid or a mixture thereof onto a strongly basic, macroreticular or gel type, water-insoluble, anionic exchange resin matrix possessing quaternary ammonium functional groups or onto a weakly basic, macroreticular or gel type, water-insoluble, anionic exchange resin matrix possessing tertiary amine or pyridine functional groups. The resin matrix is either acrylic or styrene, cross-linked with divinylbenzene. The citric acid is recovered by desorption with a water or a dilute inorganic acid, especially sulfuric acid, desorbent under desorption conditions. Concentrations of inorganic acid of about 0.01N to about 1.0N can be used in the invention, preferably 0.1 to 0.2N. These resins result in an improved separation over the neutral resins disclosed earlier. They are superior in the adsorption separation of citric acid in their increased stability to deactivation by impurities in the feed. One aspect of the invention is in the discovery that complete separation of citric acid from salts and carbohydrates is only achieved by adjusting and maintaining the pH of the feed solution lower than the first ionization constant ($pKa_1$) of citric acid (3.13). However, pHs in the range of 0.5 to 2.5 are preferred and 1.5 to 2.2 are more preferred. It is surprising that citric acid is so well separated from gluconic acid and aconitic acid since the ionization constant of gluconic acid and aconitic acid are close to that of citric acid.

The invention also relates to a process for separating citric acid from a feed mixture comprising a fermentation broth containing gluconic acid or aconitic acid or both, which process employs a water-insoluble, macroreticular or gel strongly basic anionic exchange resin possessing quaternary ammonium functional groups, or weakly basic anionic exchange resin possessing tertiary amine or pyridine functional groups said anionic exchange resin having a cross-linked acrylic or styrene resin matrix, which comprises the steps of:

(a) maintaining net fluid flow through a column of said adsorbent in a single direction, which column contains at least three zones having separate operational functions occurring therein and being serially interconnected with the terminal zones of said column connected to provide a continuous connection of said zones;

(b) maintaining an adsorption zone in said column, said zone defined by the adsorbent located between a feed input stream at an upstream boundary of said zone and a raffinate output stream at a downstream boundary of said zone;

(c) maintaining a purification zone immediately upstream from said adsorption zone, said purification zone defined by the adsorbent located between an extract output stream at an upstream boundary of said purification zone and said feed input stream at a downstream boundary of said purification zone;

(d) maintaining a desorption zone immediately upstream from said purification zone, said desorption zone defined by the adsorbent located between a desorbent input stream at an upstream boundary of said zone and said extract output stream at a downstream boundary of said zone;

(e) passing said feed mixture into said adsorption zone at adsorption conditions to effect the selective adsorption of said citric acid by said adsorbent in said adsorption zone and withdrawing the raffinate output stream comprising an organic acid such as gluconic acid, aconitic acid or a mixture thereof, and other nonadsorbed components of said fermentation broth from said adsorption zone;

(f) passing a desorbent material into said desorption zone at desorption conditions to effect the displacement of said citric acid from the adsorbent in said desorption zone;

(g) withdrawing the extract output stream comprising said citric acid and desorbent material from said desorption zone;

(h) passing at least a portion of said extract output stream to an extract separation means and therein separating at separation conditions at least a portion of said desorbent material; and, (i) periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams.

At least a portion of said raffinate stream may be passed to a separation means at separation conditions, thereby separating at least a portion of said desorbent material, to produce a raffinate product having a reduced concentration of desorbent material. Further, a buffer zone may be maintained immediately upstream from said desorption zone, said buffer zone defined as the adsorbent located between the desorbent input stream at a downstream boundary of said buffer zone and the raffinate output stream at an upstream boundary of said buffer zone.

Other aspects of the invention encompass details of feed mixtures, adsorbents, desorbents and operating conditions which are hereinafter disclosed.

DETAILED DESCRIPTION OF THE INVENTION

Figure 1:
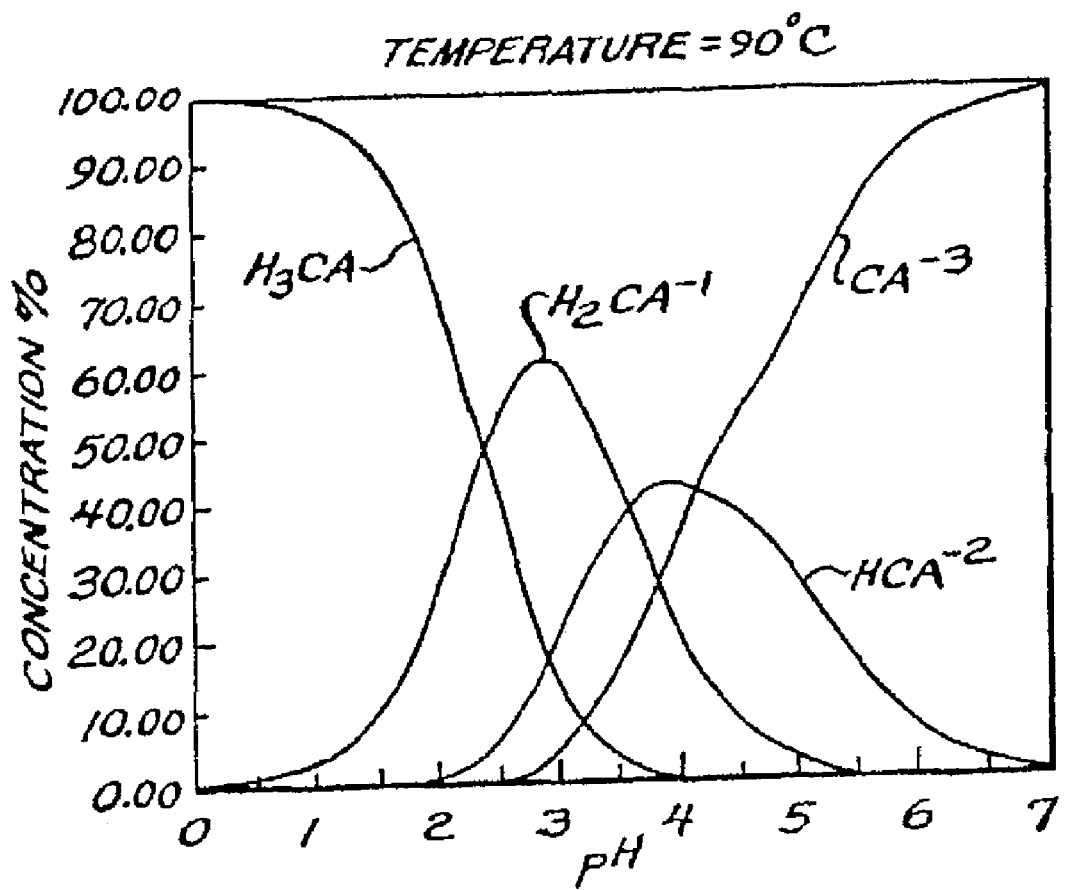
FIG. 1 is a plot of concentration of various citric acid species versus the pH of citric acid dissociation which shows the shifting of the equilibrium point of the citric acid dissociation by varying the concentration of citric acid, citrate anions and the hydrogen ion.

At the outset the definitions of various terms used throughout the specification will be useful in making clear the operation, objects and advantages of the process.

A "feed mixture" is a mixture containing one or more extract components and one or more raffinate components to be separated by the process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. In this process, citric acid is an extract component and proteins, amino acids, salts and carbohydrates are raffinate components. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators, where at least a portion of desorbent material is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high purity, citric acid product at high recoveries, it will be appreciated that an extract component is never completely adsorbed by the adsorbent. Likewise, a raffinate component is completely nonadsorbed or only slightly adsorbed by the adsorbent. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of citric acid to that of the less selectively adsorbed components will be lowest in the raffinate stream, next highest in the feed mixture, and the highest in the extract stream. Likewise, the ratio of the concentration of the less selectively adsorbed components to that of the more selectively adsorbed citric acid will be highest in the raffinate stream, next highest in the feed mixture, and the lowest in the extract stream.

The term "selective pore volume" of the adsorbent is defined as the volume of the adsorbent which selectively adsorbs an extract component from the feed mixture. The term "nonselective void volume" of the adsorbent is the volume of the adsorbent which does not selectively retain an extract component from the feed mixture. This volume includes the cavities of the adsorbent which contain no adsorptive sites and the interstitial void spaces between adsorbent particles. The selective pore volume and the nonselective void volume are generally expressed in volumetric quantities and are of importance in determining the proper flow rates of fluid required to be passed into an operational zone for efficient operations to take place for a given quantity of adsorbent. When adsorbent "passes" into an operational zone (hereinafter defined and described) employed in one embodiment of this process its nonselective void volume together with its selective pore volume carries fluid into that zone. The nonselective void volume is utilized in determining the amount of fluid which should pass into the same zone in a countercurrent direction to the adsorbent to displace the fluid present in the nonselective void volume. If the fluid flow rate passing into a zone is smaller than the nonselective void volume rate of adsorbent material passing into that zone, there is a net entrainment of liquid into the zone by the adsorbent. Since this net entrainment is a fluid present in nonselective void volume of the adsorbent, it in most instances comprises less selectively retained feed components. The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

The feed material contemplated in this invention is the fermentation product containing citric acid and gluconic acid, and possibly aconitic acid, obtained from the submerged culture fermentation of molasses by the microorganism, *Aspergillus Niger*. The fermentation product will have a composition exemplified by the following:

| | |
|---|---|
| Citric Acid | 10 mass % |
| Gluconic acid | 7 mass % |
| Salts | 6,000 ppm |
| Carbohydrates (sugars) | 1 mass % |
| Others (proteins and amino acids) | 2 mass % |
| Or | |
| Citric acid | 20 mass % |
| Gluconic acid | 1 mass % |
| Aconitic acid | (below detection limits of analytical instrumentation) |
| Salts | 6,000 ppm |
| Carbohydrates (sugars) | 1 mass % |
| Others (proteins and amino acids) | 2 mass % |

The salts will be K, Na, Ca, Mg and Fe. The carbohydrates are sugars including glucose, xylose, mannose, oligosaccharides of DP2 and DP3 plus as many as 12 or more unidentified saccharides. The composition of the feedstock may vary from that given above and still be used in the invention. However, juices such as citrus fruit juices, are not acceptable or contemplated because other materials contained therein will be adsorbed at the same time rather than citric acid alone. Johnson, J. Sci. Food Agric., Vol 33 (3) pp 287–93.

As discussed in U.S. Pat. No. 4,851,573 and U.S. Pat. No. 4,851,574, the separation of citric acid can be enhanced significantly by adjusting the pH of the feed to a level below the first ionization constant of citric acid. The first ionization constant ($pKa_1$) of citric acid is 3.13, Handbook of Chemistry & Physics, 53rd Edition, 1972–3, CRC Press, and therefore, the pH of the citric acid feed should be below 3.13. As illustrated in U.S. Pat. No. 4,851,573 and U.S. Pat. No. 4,851,574, when the pH for a 40% concentrated solution of citric acid is 2.4 or greater, for example, as in FIG. 3A (Example I) of the cited patent U.S. Pat. No. 4,851,574, citric acid "breaks through" (is desorbed) with the salts and carbohydrates at the beginning of the cycle, indicating that all the citric acid is not adsorbed In contrast, progressively less "break through" of citric acid is observed when the pH is lowered to 1.2, FIG. 3B, and to 0.9, FIG. 3C of the cited patent. The following explanation may be correct.

Looking at both the quaternary ammonium function-containing strongly basic ion exchange resins of the invention, the quaternary amine has a positive charge and can form an ionic bond with the sulfate ion. The sulfate form of quaternary ammonium anion exchange resin has a weakly basic property, which in turn, can adsorb citric acid through an acid-base interaction

(1)

(2)

(3)

Where:

P=resinous moiety

R=lower alkyl C1–3

CA=citrate ion or hydrogen bonding:

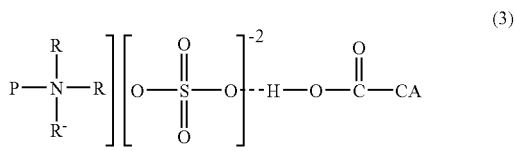

(3)

Further, looking at both the tertiary amine- and pyridine-function-containing weakly basic ion exchange resins of the present invention, the lone pair electron from the nitrogen atom can hydrogen bond to the citric aid either directly or through a sulfate ion, as for example, with a tertiary amine

(4)

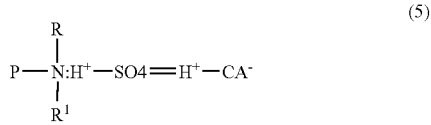

(5)

and with a pyridine function-containing resin

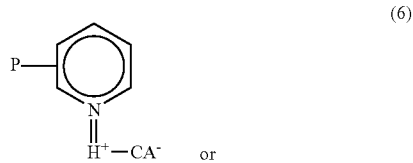

(6)

-continued

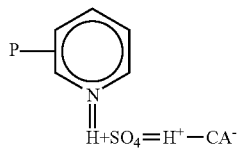

(7)

$H+SO_4 = H^+ - CA^-$

Where:

P=resinous moiety

R=lower alkyl C1–3

CA=citrate ion

At higher pH feed (3.1) there will be insufficient hydrogen ions for the hydrogen bond formation with the amine nitrogen or the sulfate ion; citric acid will not be absorbed by the resin and will "break through" with salts and carbohydrates at the beginning of the cycle. A similar explanation may be envisioned for pyridine function-containing resins.

However, even in light of this earlier discovery, the separation of citric acid from gluconic acid and or aconitic acid is surprising since the first ionization constant ($pKa_1$) of gluconic acid is 3.86 and first ionization constant ($pKa_1$) of aconitic acid is 2.8, which are both similar to that of citric acid. Keeping the pH of the feed low would not be expected to result in the resolution of citric acid from gluconic acid and or aconitic acid.

Desorbent materials used in various prior art adsorptive separation processes vary depending upon such factors as the type of operation employed. In the swing bed system, in which the selectively adsorbed feed component is removed from the adsorbent by a purge stream, desorbent selection is not as critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Desorbent materials should additionally be substances which are easily separable from the feed mixture that is passed into the process. Both the raffinate stream and the extract stream are removed from the adsorbent in admixture with desorbent material and without a method of separating at least a portion of the desorbent material the purity of the extract product and the raffinate product would not be very high, nor would the desorbent material be available for reuse in the process. It is therefore contemplated that any desorbent material used in this process will preferably have a substantially different average boiling point than that of the feed mixture to allow separation of at least a portion of the desorbent material from feed components in the extract and raffinate streams by simple fractional distillation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture. Finally, desorbent materials should also be materials which are readily available and therefore reasonable in cost. In the preferred isothermal, isobaric, liquid phase operation of the process of the invention, dilute sulfuric acid, 0.01 to 1.0N, is a particularly effective desorbent material. Also, other dilute inorganic acids such as hydrochloric acid nitric acid, phosphoric acid and water may be used as a desorbent, but may be less effective.

The prior art has also recognized that certain characteristics of adsorbents are highly desirable to the successful operation of a selective adsorption process. Such characteristics are equally important to this process. Among such characteristics are: (1) adsorptive capacity for some volume of an extract component per volume of adsorbent; (2) the selective adsorption of an extract component with respect to a raffinate component and the desorbent material; and (3) sufficiently fast rates of adsorption and desorption of an extract component to and from the adsorbent. Capacity of the adsorbent for adsorbing a specific volume of an extract component is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate an extract component of known concentration contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life. The second necessary adsorbent characteristic is the ability of the adsorbent to separate components of the feed; or, in other words, that the adsorbent possess adsorptive selectivity, ($\beta$), for one component as compared to another component. Relative selectivity can be expressed not only for one feed component as compared to another but can also be expressed between any feed mixture component and the desorbent material. The selectivity, ($\beta$), as used throughout this specification is defined as the ratio of the two components of the adsorbed phase over the ratio of the same two components in the unadsorbed phase at equilibrium conditions. Relative selectivity is shown as Equation 1 below:

$$\text{Selectivity } (\beta) = \frac{[\text{vol. Percent } C/ \text{ volume percent } D]_A}{[\text{vol. Percent } C/ \text{ volume percent } D]_U} \quad \text{Equation 1}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases. Where selectivity of two components approaches 1.0 there is no preferential adsorption of one component by the adsorbent with respect to the other; they are both adsorbed (or nonadsorbed) to about the same degree with respect to each other. As the fl becomes less than or greater than 1.0 there is a preferential adsorption by the adsorbent for one component with respect to the other. When comparing the selectivity by the adsorbent of one component C over component D, a β larger than 1.0 indicates preferential adsorption of component C within the adsorbent. A β less than 1.0 would indicate that component D is preferentially adsorbed leaving an unadsorbed phase richer in component C and an adsorbed phase richer in component D. Ideally desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity, the easier the separation is to perform. Higher selectivities permit a smaller amount of adsorbent to be used. The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber comprising a straight or helical column of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent, is injected for a duration of several minutes. Desorbent flow is resumed, and the tracer and the extract component or the raffinate component (or both) are eluted as in a liquid-solid chromatographic operation. The effluent can be analyzed on-stream or, alternatively, effluent samples can be collected periodically and later analyzed.

From information derived from the test adsorbent, performance can be in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (β), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of desorbent pumped during this time interval.

To further evaluate promising adsorbent systems and to translate this type of data into a practical separation process requires actual testing of the best system in a continuous countercurrent liquid-solid contacting device. The general operating principles of such a device have been previously described and are found in U.S. Pat. No. 2,985,589. A specific laboratory size apparatus utilizing these principles is described in U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and the raffinate and extract streams are being withdrawn through two more. All remaining access lines are inactive and when the position of the distributing valve is advanced by one index, all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W. Neuzil, D. J. Korous, and D. H. Rosback presented at the American Chemical Society, Los Angeles, Calif., Mar. 28 through Apr. 2, 1971.

Adsorbents to be used in the process of this invention will comprise strongly or weakly basic anion exchange resins possessing quaternary ammonium, tertiary amine, or pyridine functionality in a cross-linked polymeric matrix, e.g., divinylbenzene cross-linked acrylic or styrene resins. They are especially suitable when produced in bead form and have a high degree of uniform polymeric porosity and exhibit chemical and physical stability. In the instant case, the resins can be gelular (or "gel-type") or "macroreticular" as the term is used in some recent literature, namely Kunin and Hetherington, A Progress Report on the Removal of Colloids From Water by Macroreticular Ion Exchange Resins, paper presented at the International Water Conference, Pittsburg, Pa., October 1969, reprinted by Rohm & Haas Co. In adsorption technology, "the term microreticular refers to the gel structure per se, size of the pores which are of atomic dimensions and depend upon the swelling properties of the gel" while "macroreticular pores and true porosity refer to structures in which the pores are larger than atomic distances and are not part of the gel structure. Their size and shape are not greatly influenced by changes in the environmental conditions such as those that result in osmotic pressure variations" while the dimensions of gel structure are "markedly dependent upon the environmental conditions." In "classical adsorption" "the terms microporous and macroporous normally refer to those pores less than 20 A and greater than 200 A, respectively. Pores of diameters between 20 A and 200 A are referred to as transitional pores." The authors selected the term "macroreticular", instead, to apply to the new ion exchange resins used in this invention, which "have both a microreticular as well as a macroreticular pore structure. The former refers to the distances between the chains and crosslinks of the swollen gel structure and the latter to the pores that are not part of the actual chemical structure. The macroretical portion of structure may actually consist of micro, macro, and transitional-pores depending upon the pore size distribution." (Quotes are from page 1 of the Kunin et al. article). The macroreticular structured adsorbents also have good resistance to attrition (not common to conventional macroreticular resins). In this application, therefore, all reference to "macroreticular" indicates adsorbent of the types described above having the dual porosity defined by Kunin and Hethesing. "Gel" and "gel-type" are used in their conventional sense.

Adsorbents such as just described are manufactured by the Rohm and Haas Company, and sold under the trade name "Amberlite." The types of Amberlite polymers known to be effective for use by this invention are referred to in Rohm and Haas Company literature as Amberlite IRA 400 and 900 series adsorbents and XE-275 (IRA-35), IRA-68 adsorbents and described in the literature as "insoluble in all common solvents and having open structure for effective adsorption and desorption of large molecules without loss of capacity, due to organic fouling." Also suitable are AG1, AG2, AGMP-1, AG3-X4A and AG4-X4 resins manufactured by Bio Rad and comparable resins sold by Dow Chemical Co., such as Dowex 1, 2, 11, MSA-1, MSA-2, 66, and Dow experimental resins made in accordance with U.S. Pat. No. 4,031,038 and U.S. Pat. No. 4,098,867. Also useful in this invention are the so-called intermediate base ion exchange which are mixtures of strong and weak base exchange resins. Among these are the following commercially available resins: Bio-Rex 5 (Bio-Rad 1); Amberlite IRA-47 and Duolite A-340 (both Rohm & Haas). For example, they may be useful where a basic ion exchange resin is needed which is not as basic as the strong base resins, or one which is more basic than the weakly basic resins.

The various types of polymeric adsorbents of these classes available will differ somewhat in physical properties such as porosity volume percent, skeletal density and nominal mesh sizes, and perhaps more so in surface area, average pore diameter and dipole moment. The preferred adsorbents will have a surface area of 10–2000 square meters per gram and preferably from 100–1000 $m^2/g$. Specific properties of the materials listed above can be found in company literature and technical brochures, such as those in the following Table 1. Others of the general class are also available.

TABLE 1

Properties of Adsorbents

| Adsorbent | Matrix Type | Reference to Company Literature |
|---|---|---|
| IRA 458 Acrylic (Rohm & Haas) | gel-type | Amberlite Ion Exchange Resins 1986 & Technical Bulletin IE-207-74 84 |
| IRA 958 | Acrylic macroporous | Technical Bulletin and Material Safety Data Sheet are available |
| IRA 900 | Polystyrene macroporous | Technical Bulletin is available and Amberlite Ion Exchange Resins, IE-100-66. |
| IRA 904 | Polystyrene macroporous | Technical Bulletin, 1979 and IE-208/74, January 1974 |
| IRA 910 | Polystyrene macroporous | Technical Bulletin, 1979 and IE-101-66, May 1972 |
| IRA 400 | Polystyrene | Amberlite Ion Exchange Resins, October, September 1976, |
| IRA 400 | macroporus | April 1972 and IE-69-62, October 1976 |
| IRA 410 | Polystyrene gel-type | Amberlite Ion Exchange Resins IE-72-63, August 1970 |
| AG 1 (Bio Rad) | Polystyrene gel-type | Chromatography Electrophoresis Immunochemistry Molecular Biology HPLC, Price List M April 1987 |
| AG 2 | Polystyrene gel-type | Chromatography Electrophoresis Immunochemistry Molecular Biology HPLC, Price List M April 1987 |
| AG-MP-1 | Polystyrene macroporous | Chromatography Electrophoresis Immunochemistry Molecular Biology HPLC, Price List M April 1987 |
| Bio Rex 5 (Bio Rad) | Mixture of strong base and weak base resins (e.g. Ag-2 and AG-3 or AG-4) | Chromatography Electrophoresis Immunochemistry Molecular Biology HPLC, Price List M April 1987 |
| AG3-4A (Bio Rad) | Polystyrene | Chromatography Electrophoresis Immunochemistry Molecular Biology - HPLC - Price List M April 1987 (Bio-Rad) |
| AG4-X4 | Acrylic | Chromatography Electrophoresis Immunochemistry Molecular Biology - HPLC - Price List M April 1987 (Bio-Rad) |
| Dow | Polystyrene Experimental Resins | U.S. Pat. Nos. 4,031,038 and 4,098,867 |

TABLE 1-continued

Properties of Adsorbents

| Adsorbent | Matrix Type | Reference to Company Literature |
| --- | --- | --- |
| Dowex 66 | Polystyrene | Material Safety Data Sheet Printed Feb. 17, 1987 (Dow Chemical USA) |
| IRA-35 (XE-275) | Acrylic | Amberlite Ion Exchange Resins (XE-275) Rohm & Haas Co. 1975 |
| IRA-68 | Acrylic | Amberlite Ion Exchange Resins Amberlite IRA-68 Rohm & Haas Co. April 1977 |

Applications for Amberlite polymeric adsorbents suggested in the Rohm and Haas Company literature include decolorizing pulp mill bleaching effluent, decolorizing dye wastes and removing pesticides from waste effluent. There is, of course, no hint in the literature of my surprising discovery of the effectiveness of Amberlite polymeric adsorbents in the separation of citric acid from *Aspergillus-Niger* fermentation broths.

The adsorbent may be employed in the form of a dense compact fixed bed which is alternatively contacted with the feed mixture and desorbent materials. In the simplest embodiment of the invention, the adsorbent is employed in the form of a single static bed, in which case the process is only semicontinuous. In another embodiment a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving bed or simulated moving bed countercurrent flow systems, however, have a much greater separation efficiency than fixed adsorbent bed systems and are therefore preferred. In the moving bed or simulated moving bed processes the adsorption and desorption operations are continuously taking place which allows both continuous production of an extract and a raffinate stream and the continual use of feed and desorbent streams. One preferred embodiment of this process utilizes what is known in the art as the simulated moving bed countercurrent flow system. The operating principles and sequence of such a flow system are described in U.S. Pat. No. 2,985,589 incorporated herein by reference. In such a system it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divided the adsorbent chamber into separate zones, each of which has a different function. In this embodiment of my process it is generally necessary that three separate operational zones be present in order for the process to take place although in some instances an optional fourth zone may be used.

The adsorption zone, zone 1, is defined as the adsorbent located between the feed inlet stream and the raffinate outlet stream. In this zone, the feedstock contacts the adsorbent, extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the nonselective void volume of the adsorbent of any raffinate material carried into zone 2 by shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating extract stream removed from zone 3. In the instances which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. No. 3,040,777 and U.S. Pat. No. 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances one of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column, the design and operation of which is well-known to the separation art.

Reference can be made to U.S. Pat. No. 2,985,589, which is hereby incorporated herein by reference, for further explanation of the simulated moving bed countercurrent process flow scheme.

Although both liquid and vapor phase operations can be used in many adsorptive separation processes, liquid-phase operation is preferred for this process because of the lower temperature requirements and because of the higher yields of extract product than can be obtained with liquid-phase operation over those obtained with vapor-phase operation. Adsorption conditions will include a temperature range of from about 20° C. to about 200° C. with about 50° C. to about 90° C. being more preferred and a pressure range of from about atmospheric to about 500 psig (3450 kPa gauge) being more preferred to ensure liquid phase. Desorption conditions will include the same range of temperatures and pressures as used for adsorption conditions.

The size of the units which can utilize the process of this invention can vary anywhere from those of pilot plant scale (see for example U.S. Pat. No. 3,706,812, incorporated herein by reference) to those of commercial scale and can range in flow rates from as little as few cc an hour up to many thousands of gallons per hour.

The following examples are presented to illustrate the selectivity relationship that makes the process of my invention possible. The examples are not intended to unduly restrict the scope and spirit of claims.

EXAMPLE 1

In this example, a pulse test was run with a macroporous, strongly basic anionic exchange adsorbent, IRA-958, possessing quaternary ammonium functions and an acrylic resin matrix cross-linked with divinylbenzene matrix, to determine the ability of the adsorbent to separate citric acid from gluconic acid and other components of the fermentation mixture of carbohydrates (DP1, DP2, DP3, including glucose, xylose, arabinose and raffinose) and ions of salts, including $Na^+$, $K^+$, $Mg^{++}$, $Ca^{++}$, $Fe^{+++}$, $Cl^-$, $SO_4^=$, $PO_4^\equiv$ and $NO_3^-$, amino acids and proteins at a pH of 2.2. P is acrylic cross-linked with divinylbenzene. The test was run at a temperature of 60° C. Citric acid was desorbed with 0.1N solution of sulfuric acid. The fermentation feed mixture had the following composition:

| Feed Composition | Mass Percent |
| --- | --- |
| Citric Acid | 15.13 |
| Gluconic acid | 7.29 |
| Salts | 1.5 |
| ($K^+$, $Na^+$, $Ca^{++}$, $Mg^{++}$, $Fe^{+++}$) | |
| Carbohydrates (Sugars) | Unknown |
| Others | 1.12 |
| ($Cl^-$, $SO_4^-$, $PO_4^\equiv$, $NO_3^-$, | |
| amino acids and proteins | 0.05 |
| Water | 75.0 |

Retention volumes and separation factor were obtained using the pulse test apparatus and procedure previously described. Specifically, the adsorbent was tested in a 70 cc straight column using the following sequence of operations for the pulse test. Desorbent material was continuously run upwardly through the column containing the adsorbent at a nominal liquid hourly space velocity (LHSV) of about 1.0. Void volume was determined by observing the volume of desorbent required to fill the packed dry column. At a convenient time, the flow of desorbent material was stopped, and a 5 cc sample of feed mixture was injected into the column via a sample loop and the flow of desorbent material was resumed. Samples of the effluent were automatically collected in an automatic sample collector and later analyzed for salts and citric acid by chromatographic analysis. The extract and raffinate components were not analyzed separately for the other feed components, e.g., carbohydrates, proteins, etc. which were contained therein. From the analysis of these samples, peak envelope concentrations were developed for the feed mixture components. The retention volume for the citric acid was calculated by measuring the distance from the midpoint of the net retention volume of the salt envelope as the reference point to the midpoint of the citric acid envelope. The separation factor, β, is calculated from the ratio of the retention volumes of the two compounds. The results for the pulse test are shown below:

| FIG. No. | Resin | Feed Component | NRV | β |
|---|---|---|---|---|
| 2 | IRA-958 | Salts | 0 | 0 |
| | | Citric Acid | 28.0 | 1 |
| | | Carbohydrate | 0.3 | 93.33 |
| | | Gluconic acid | 6.1 | 4.60 |
| | | Unknowns A | 6.0 | 4.71 |
| | | Unknowns B | 9.5 | 2.94 |

Figure 2:
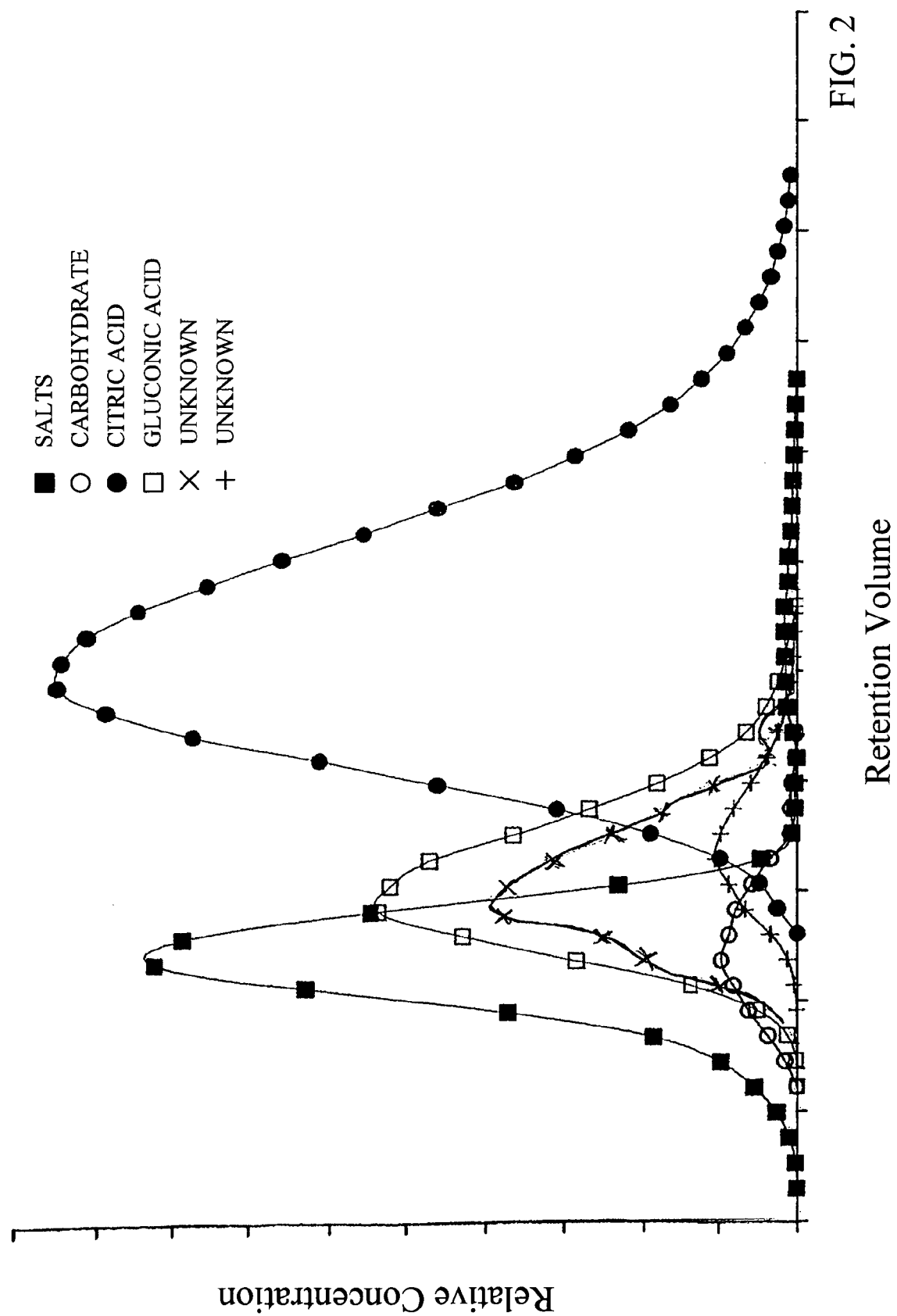
FIG. 2 is the plot of the pulse test in Example I using quaternary amine functionality in a cross-linked acrylic resin matrix to separate citric acid from a feed at a pH of 2.2 containing 15% citric acid and 7% gluconic acid, desorbed with dilute sulfuric acid.

The results are also shown in FIG. 2 where it is clear that citric acid is satisfactorily separated from gluconic acid and other fermentation broth components in the process.

EXAMPLE 2

Another pulse test was run with the same macroporous, strongly basic anionic exchange adsorbent, IRA-958, and the same conditions as in Example I with the exception of 10 cc sample of feed mixture was injected into the column via a sample loop instead of 5 cc. In addition, the fermentation mixture in this example also contained aconitic acid.

| Feed Composition | Mass Percent |
|---|---|
| Citric Acid | 20 |
| Aconitic acid | (below detection limits of analytical instrumentation) |
| Salts ($K^+$, $Na^+$, $Ca^{++}$, $Mg^{++}$, $Fe^{+++}$) | 3.34 |
| Carbohydrates (Sugars) | Unknown |
| Others ($Cl^-$, $SO_4^=$, $PO_4^\equiv$, $NO_3^-$, amino acids and proteins) | 1 |
| Water | 75.66 |

Analysis of the feed did not result in quantifying the amount of aconitic acid since the amount was below the detection limits of the analytical instrumentation. Retention volumes and separation factor were obtained using the pulse test apparatus and procedure previously described. Specifically, the adsorbent was tested in a 70 cc straight column using the following sequence of operations for the pulse test. Desorbent material was continuously run upwardly through the column containing the adsorbent at a nominal liquid hourly space velocity (LHSV) of about 1.0. Void volume was determined by observing the volume of desorbent required to fill the packed dry column. At a convenient time, the flow of desorbent material was stopped, and a 10 cc sample of feed mixture was injected into the column via a sample loop and the flow of desorbent material was resumed. Samples of the effluent were automatically collected in an automatic sample collector and later analyzed for salts and citric acid by chromatographic analysis. The extract and raffinate components were not analyzed separately for the other feed components, e.g., carbohydrates, proteins, etc. which were contained therein. From the analysis of these samples, peak envelope concentrations were developed for the feed mixture components. The retention volume for the citric acid was calculated by measuring the distance from the midpoint of the net retention volume of the salt envelope as the reference point to the midpoint of the citric acid envelope. The separation factor, β, is calculated from the ratio of the retention volumes of the two compounds. The results for the pulse test are shown below.

| FIG. No. | Resin | Feed Component | NRV | β |
|---|---|---|---|---|
| 3 | IRA-958 | Salts | 0 | 0 |
| | | Carbohydrate | 4.9 | 8.87 |
| | | Citric Acid | 33.8 | 1 |
| | | Aconitic acid | 20.4 | 1.70 |
| | | Unknowns | 11.5 | 1.01 |

Figure 3:
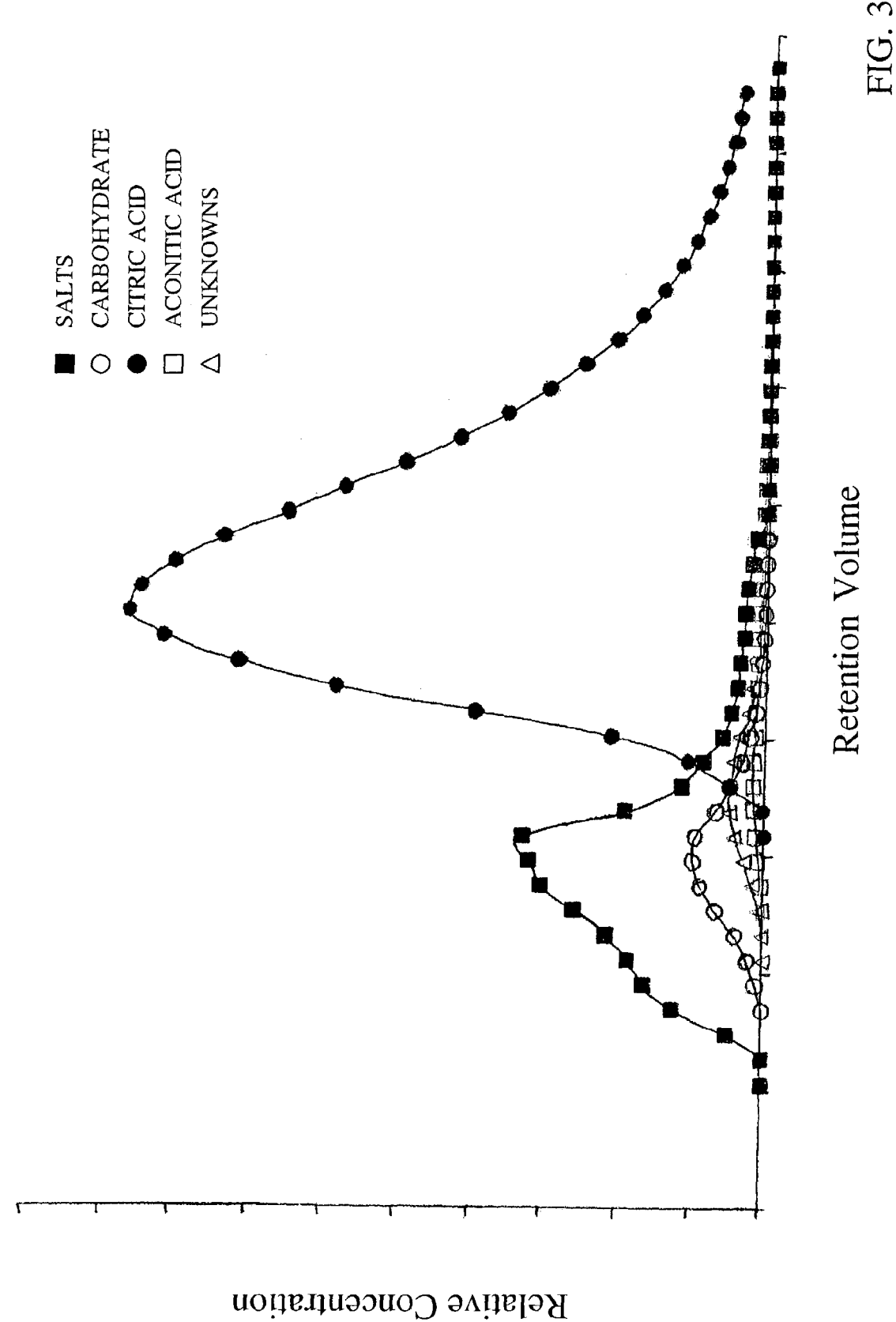
FIG. 3 is the plot of the pulse test in Example II using quaternary amine functionality in a cross-linked acrylic resin matrix to separate citric acid from a feed at a pH of 2.2 containing 20% citric acid and aconitic acid (below detection limits of analytical instrumentation), desorbed with dilute sulfuric acid.

The results are also shown in FIG. 3 where it is clear that citric acid is satisfactorily separated from gluconic acid, aconitic acid, and other fermentation broth components in the process.

What is claimed is:

1. An adsorptive separation process comprising contacting a fermentation broth containing at least citric acid and gluconic acid, with a water-insoluble basic anionic exchange resin selected from the group consisting of a strongly basic anionic exchange resin possessing quaternary amine functional groups and having a cross-linked, copolymeric styrene or acrylic resin matrix, and a weakly basic anionic exchange resin possessing tertiary amine or pyridine functional groups and having cross-linked acrylic or styrene resin matrix, wherein the water-insoluble basic anionic exchange resin is in the sulfate form, at adsorption conditions selected to selectively adsorb said citric acid, said adsorption conditions including pH lower than the first ionization constant ($pKa_1$) of citric acid, and desorbing the citric acid with a desorbent comprising water or a dilute inorganic acid at desorption conditions.

2. The process of claim 1 further comprising recovering the citric acid.

3. The process of claim 1 wherein said desorbent is dilute sulfuric acid.

4. The process of claim 1 further characterized in that said adsorption and desorption conditions include a temperature within the range of from about 20° C. to about 200° C. and a pressure within the range of from about atmospheric to about 500 psig (3450 kPa gauge).

5. The process of claim 1 further characterized in that said desorbing is effected in the liquid phase with dilute sulfuric acid.

6. The process of claim 1 further characterized in that the pH of said feed mixture is lower than the first ionization constant ($pKa_1$) of citric acid.

7. The process of claim 1 further characterized in that said strongly basic anionic exchange resin has a quaternary amine functional group and said matrix is a cross-linked acrylic resin.

8. The process of claim 1 further characterized in that said weakly basic anionic exchange resin has a pyridine functional group and said matrix is a cross-linked polystyrene resin.

9. The process of claim 1 further characterized in that said weakly basic anionic exchange resin has a tertiary amine functional group and said matrix is a cross-linked acrylic resin.

10. The process of claim 1 further characterized in that said anionic exchange resin has a surface area of at least 10 $m^2/g$.

11. The process of claim 1 wherein said fermentation broth comprises citric acid, gluconic acid, carbohydrates, and salts.

12. The process of claim 1 wherein said anionic exchange resin is macroreticular.

13. The process of claim 1 wherein said anionic exchange resins is gelular.

14. A process for separating citric acid from a feed mixture comprising a fermentation broth containing at least citric acid and gluconic acid, said process comprising: employing a water-insoluble basic anionic exchange resin adsorbent selected from the group consisting of a strongly basic anionic exchange resin possessing quaternary amine functional groups and having a cross-linked, copolymeric styrene or acrylic resin matrix, and a weakly basic anionic exchange resin possessing tertiary amine or pyridine functional groups and having cross-linked acrylic or styrene resin matrix, wherein the water-insoluble basic anionic exchange resin is in the sulfate form;
(a) maintaining net fluid flow through a column of said adsorbent in a single direction, which column contains at least three zones having separate operational functions occurring therein and being serially interconnected with the terminal zones of said column connected to provide a continuous connection of said zones;
(b) maintaining an adsorption zone in said column, said zone defined by the adsorbent located between a feed input stream at an upstream boundary of said zone and a raffinate output stream at a downstream boundary of said zone;
(c) maintaining a purification zone immediately upstream from said adsorption zone, said purification zone defined by the adsorbent located between an extract output stream at an upstream boundary of said purification zone and said feed input stream at a downstream boundary of said purification zone;
(d) maintaining a desorption zone immediately upstream from said purification zone, said desorption zone defined by the adsorbent located between a desorbent input stream at an upstream boundary of said zone and said extract output stream at a downstream boundary of said zone;
(e) passing said feed mixture into said adsorption zone at adsorption conditions to effect the selective adsorption of said citric acid by said adsorbent in said adsorption zone and withdrawing the raffinate output stream comprising at least gluconic acid from said adsorption zone;
passing a desorbent material comprising water or a dilute inorganic acid into said desorption zone at desorption conditions to effect the displacement of said citric acid from the adsorbent in said desorption zone;
(g) withdrawing the extract output stream comprising said citric acid and desorbent material from said desorption zone;
(h) passing at least a portion of said extract output stream to an extract separation means and therein separating at separation conditions at least a portion of said desorbent material; and,
(i) periodically advancing through said column of adsorbent in a downstream direction with respect to fluid flow in said adsorption zone the feed input stream, raffinate output stream, desorbent input stream, and extract output stream to effect the shifting of zones through said adsorbent and the production of extract output and raffinate output streams.

15. The process of claim 14 further comprising the step of passing at least a portion of said raffinate output stream to a raffinate separation means and therein separating at separation conditions at least a portion of said desorbent material to produce a raffinate product having a reduced concentration of desorbent material.

16. The process of claim 14 further comprising the step of maintaining a buffer zone immediately upstream from said desorption zone, said buffer zone defined as the adsorbent located between the desorbent input stream at a downstream boundary of said buffer zone and the raffinate output stream at an upstream boundary of said buffer zone.

17. The process of claim 14 further characterized in that said adsorption conditions and desorption conditions include a temperature within the range of from about 20° C. to about 200° C. and a pressure within the range of from about atmospheric to about 500 psig (3450 kPa gauge) to ensure liquid phase.

18. The process of claim 14 wherein said desorbent material is sulfuric acid at a concentration in the range from about 0.01N to about 1.0N.

* * * * *